(12) United States Patent
Van Vlasselaer et al.

(10) Patent No.: US 6,197,579 B1
(45) Date of Patent: Mar. 6, 2001

(54) CELL WASHING DEVICE AND METHOD

(75) Inventors: Peter Van Vlasselaer; Shirin W. Hasan, both of Sunnyvale, CA (US)

(73) Assignee: Dendreon Corporation, Seattle, WA (US)

( * ) Notice: Subject to any disclaimer, the term of this patent is extended or adjusted under 35 U.S.C. 154(b) by 0 days.

(21) Appl. No.: 09/118,326

(22) Filed: Jul. 17, 1998

Related U.S. Application Data

(63) Continuation-in-part of application No. 08/800,687, filed on Feb. 14, 1997, now abandoned.

(51) Int. Cl.$^7$ .................................................. C12N 5/00
(52) U.S. Cl. ...................... 435/325; 210/781; 210/782; 435/2; 435/243; 435/308.1
(58) Field of Search ................. 435/2, 325, 243, 435/308.1; 210/781, 782

(56) References Cited

U.S. PATENT DOCUMENTS

| | | |
|---|---|---|
| 928,552 | 7/1909 | Shimer . |
| 956,708 | 5/1910 | Jensen . |
| 1,597,513 | 8/1926 | Dever . |
| 3,407,812 | 10/1968 | Lucas . |
| 3,452,924 | 7/1969 | Schlutz . |
| 3,468,474 | 9/1969 | Shoblom et al. . |
| 3,561,672 | 2/1971 | Schlutz et al. . |
| 3,635,370 | 1/1972 | Romanauskas . |
| 3,674,197 | 7/1972 | Mitchell et al. . |
| 3,858,795 | 1/1975 | Joyce . |
| 3,877,634 | 4/1975 | Rohde et al. . |
| 3,897,902 | 8/1975 | Yanez, Jr. . |
| 3,914,985 | 10/1975 | von Behrens . |
| 3,976,579 | 8/1976 | Bennett . |
| 4,106,907 | 8/1978 | Charlton et al. . |
| 4,114,803 | 9/1978 | Romanauskas . |
| 4,179,339 | 12/1979 | Sogi et al. . |
| 4,222,513 | 9/1980 | Webster et al. . |
| 4,241,005 | 12/1980 | Rothschild et al. . |
| 4,268,393 | 5/1981 | Persidsky et al. . |
| 4,290,300 | 9/1981 | Carver . |
| 4,364,903 | 12/1982 | Bittings . |
| 4,426,295 | 1/1984 | Evans et al. . |
| 4,487,696 | 12/1984 | Ferrara . |
| 4,522,713 | 6/1985 | Nussbaumer et al. . |
| 4,576,185 | 3/1986 | Proud et al. . |
| 4,620,794 | 11/1986 | Leka . |
| 4,690,670 | 9/1987 | Nielsen . |
| 4,698,311 | 10/1987 | Hall et al. . |
| 4,902,270 | 2/1990 | Comeau et al. . |
| 4,927,750 | 5/1990 | Dorn . |
| 4,990,129 | 2/1991 | Nielsen . |
| 5,047,004 | 9/1991 | Wells . |
| 5,178,602 | 1/1993 | Wells . |
| 5,244,635 | 9/1993 | Rabson et al. . |
| 5,253,551 | 10/1993 | DeVaughn . |
| 5,282,982 | 2/1994 | Wells . |
| 5,310,527 | 5/1994 | Romanauskas et al. . |
| 5,405,308 | 4/1995 | Headly et al. . |
| 5,474,687 | 12/1995 | Van Vlasselaer . |
| 5,530,553 | 6/1996 | Hsia et al. . |
| 5,663,051 | 9/1997 | Vlasselaer . |
| 5,789,148 | 8/1998 | Van Vlasselaer et al. . |
| 5,840,502 | 11/1998 | Van Vlasselaer . |

FOREIGN PATENT DOCUMENTS

| | | |
|---|---|---|
| 4445030 | 6/1996 | (DE) . |
| 137292 | 1/1985 | (EP) . |
| 2554241 | 5/1985 | (FR) . |
| 855788 | 12/1960 | (GB) . |
| WO93/14869 | 8/1993 | (WO) . |
| WO96/07097 | 3/1996 | (WO) . |

OTHER PUBLICATIONS

International Search Report for related PCT Application No: US98/02661.

*Primary Examiner*—Leon B. Lankford, Jr.
(74) *Attorney, Agent, or Firm*—Jeffery D. Frazier; Iota Pi Law Group

(57) ABSTRACT

Disclosed is a cell washing device and method of washing cells that utilizes the device. The device is particularly designed for sterile transfer of cells from a primary centrifuge tube and for maintaining the cells in a sterile environment during subsequent washing steps. The device is configured to provide for decantation of a supernatant by inversion without appreciable loss of a selected population of lower density cells from the pellet during the washing procedure.

18 Claims, 11 Drawing Sheets

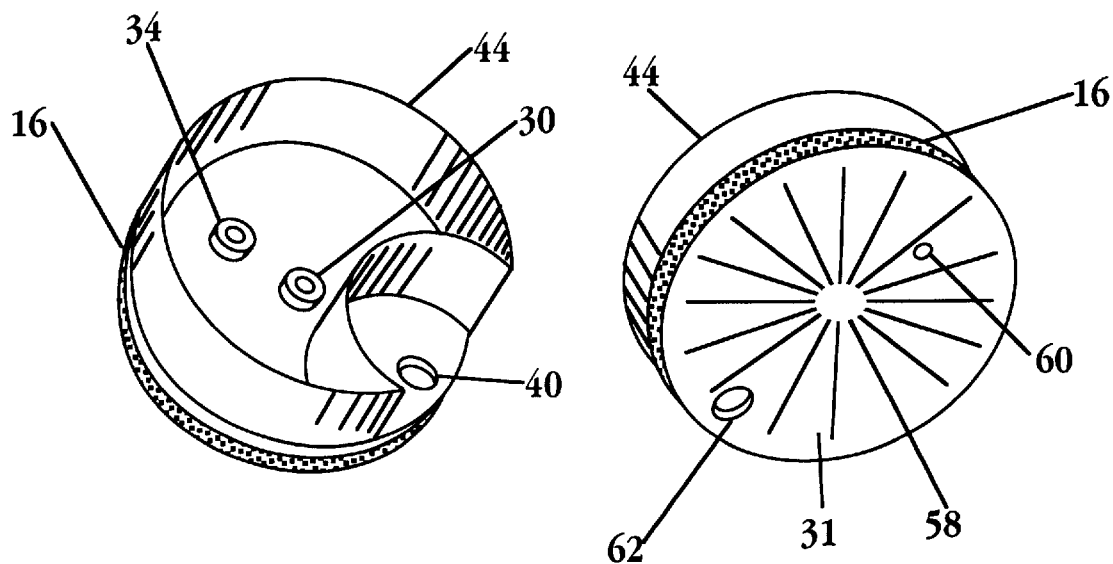
Fig. 2A  Fig. 2B
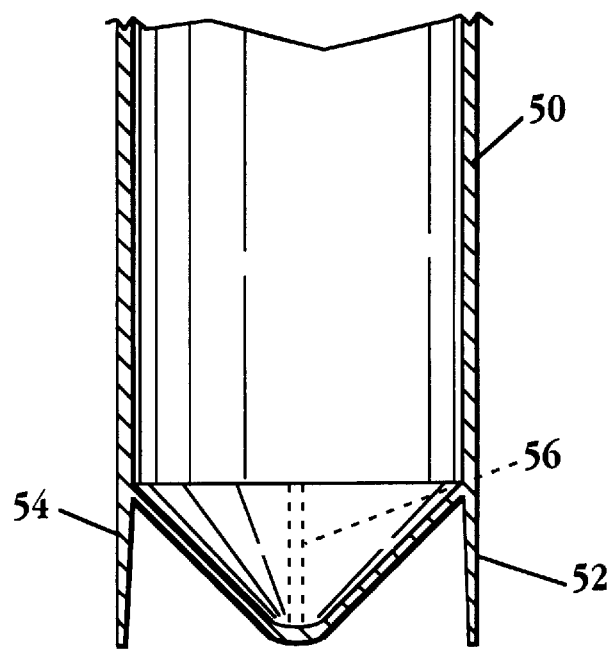
Fig. 3

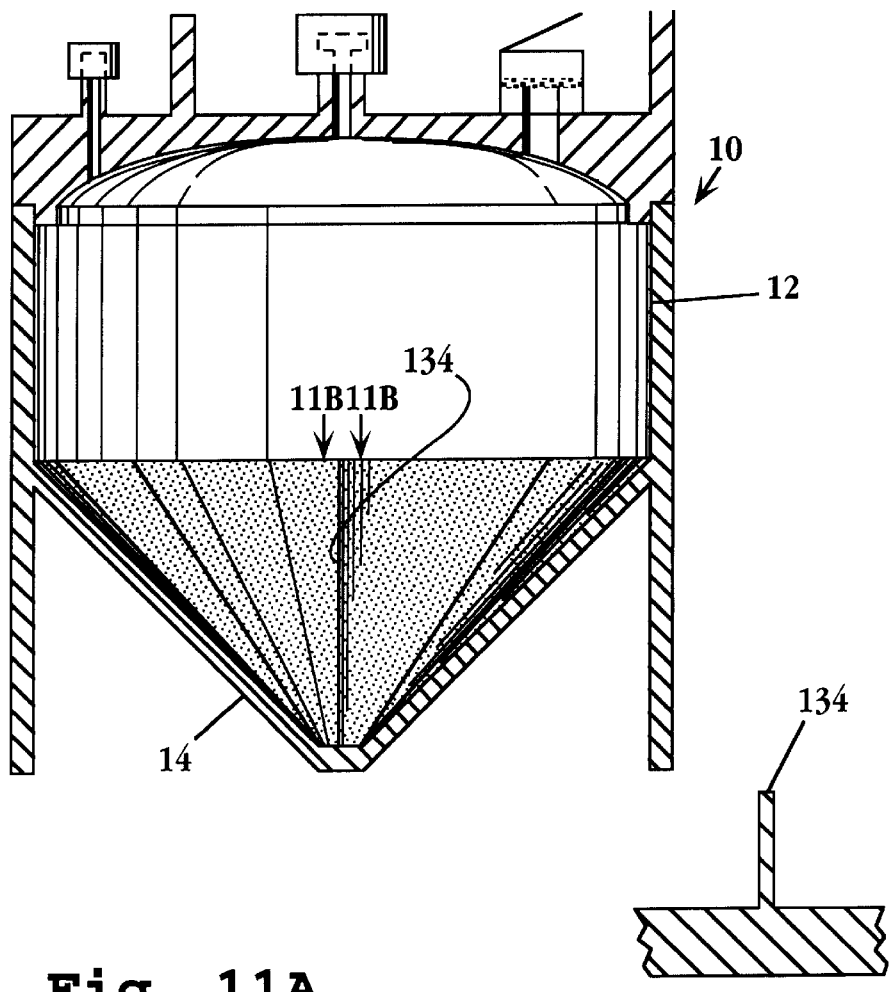
Fig. 11A
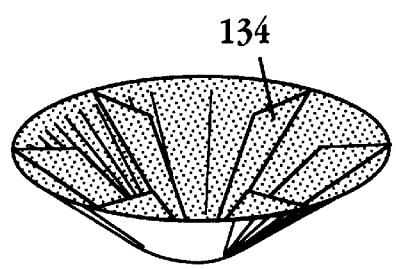
Fig. 11B
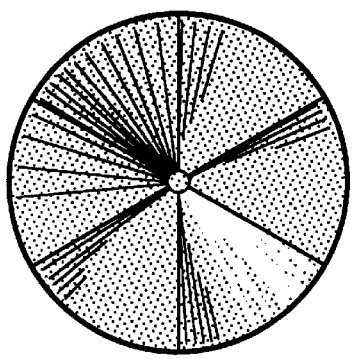
Fig. 11C     Fig. 11D

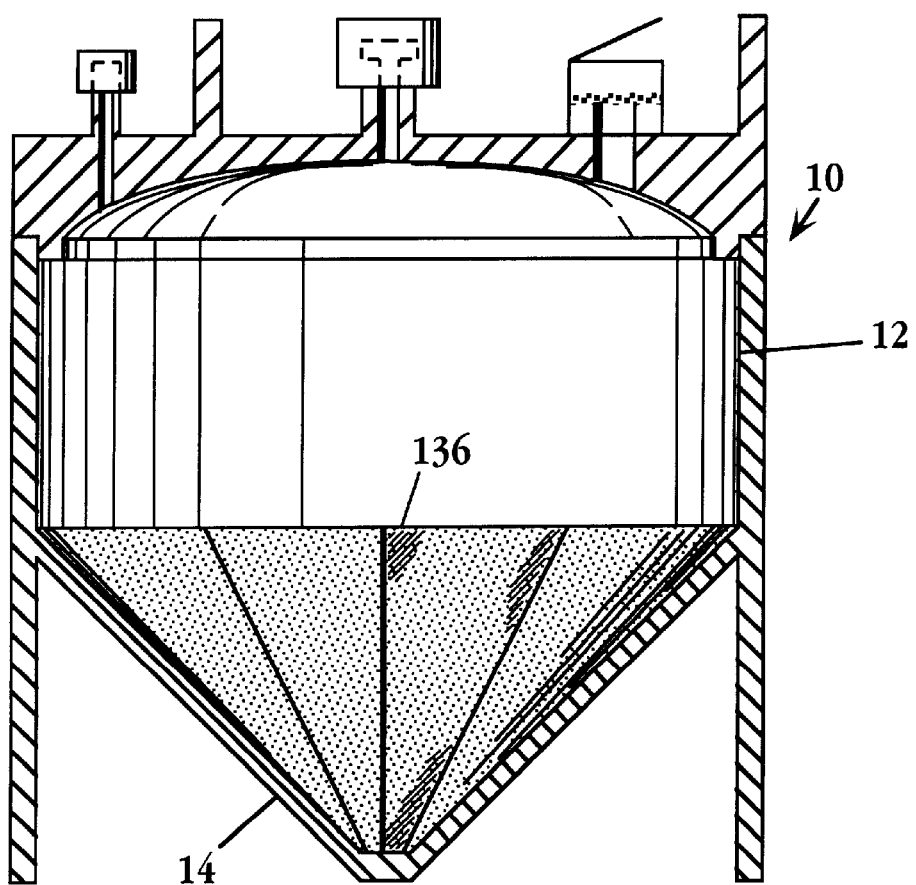
Fig. 12A
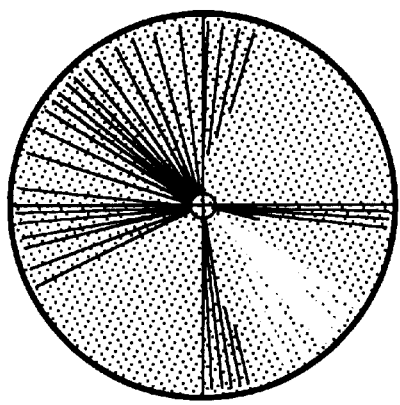
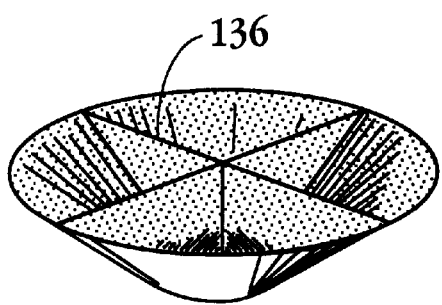
Fig. 12B  Fig. 12C

CELL WASHING DEVICE AND METHOD

This application is a continuation in part of U.S. patent application Ser. No. 08/800,687, filed Feb. 14, 1997, now abandoned which is incorporated herein by reference it its entirety.

FIELD OF THE INVENTION

The invention is concerned with centrifugable devices that are suitable for washing isolated cells. The invention is also concerned with a method of washing certain rare cell populations using such containers.

BACKGROUND OF THE INVENTION

Advances in cell separation technology have spawned therapeutic methods in which a subject's cells can be removed from the bloodstream or bone marrow and fractionated to provide specific cell types for re-introduction into the subject or of a recipient patient. For example, U.S. Pat. No. 5,840,502, filed Aug. 31, 1994, describes methods for enriching cell fractions and indications for use of such fractions.

In enriching a cell fraction from a cell suspension, it is many times desirable to add reagents, such as cell-specific antibodies or buffering agents, to the cell suspension as part of the fractionation procedure. Such reagents must be removed before re-introduction of the cells into a patient. Alternatively or in addition, it is many times desirable to change the ionic conditions of the cells prior to use of the cells, such as in the therapeutic indications referred to above.

As such cell fractionation procedures become routine in the clinical setting, it is desirable that handling and manipulation of the cells be minimized, so that cells can be processed in a minimum amount of time and with a minimum amount of exposure to potential contamination.

Typically, isolated cells are washed by either resuspending the cells in the same centrifuge tube or bag in which they were originally centrifuged or by transferring the cells to a different centrifugable container. Cells are resuspended in the wash buffer and re-centrifuged at relatively low centrifugal forces (approx. 1000×g). The cells form a soft pellet from which the wash supernatant must be removed prior to subsequent washings or resuspension in the final buffer.

Removal of supernatant can be effected either by decantation or by gentle aspiration. Decantation, while a relatively fast operation, often results in cell loss, differentially depleting those cells having relatively low specific gravities and which sediment on the top of the pellet. For this reason, decantation has generally not been considered to be a reliable means for removing supernatants from cells, particularly when such cells have relatively low specific gravities.

Aspiration, on the other hand, is labor-intensive, and unless careful attention is given to each individual tube, may also selectively result in loss of "lighter" cells from the pellet into the discarded washing solution. In addition, aspiration requires introduction of a probe into the cell container. This may also introduce contamination into the container.

One attempt to solve the foregoing problems is found in U.S. Pat. No. 5,047,004 (Wells) which describes an automatic decanting centrifuge in which swinging buckets are locked in an extended angle following centrifugation, to effect gravity decantation of the fluid therein. This system, while providing relative ease and automaticity to the decantation process, necessarily exposes the cells to contamination, by its open top design. Moreover, there is no provision for ensuring that the more slowly sedimenting "light" cells are retained in the pellet.

U.S. Pat. No. 5,474,687 describes a method and specialized tube for enriching an exemplified fraction of rare cells, $CD34^+$ hematopoietic progenitor cells, in a single-step density gradient, by selectively collecting the "light" cells that migrate to the cell solution-density gradient interface. However, these cells must be pelleted and washed prior to use. Such pelleting and washing is typically carried out at relatively low speeds (500–1000×g) in preparative centrifuge tubes that are available commercially. Using such conventional washing methods, it has been found that the $CD34^+$ cells are differentially lost during the washing procedure, since they are "light" cells that tend to sediment to the top of the pellet formed during the washing process.

The present invention provides a cell washing device that overcomes the problems just described. The device includes a tube with a sealable cap or lid that provides for sterile transfer and handling of cells. Specifically, cells or liquid medium can be added to the tube by means of a sterile port which traverses the cap. In addition, according to an important feature of the invention, wash supernatant can be decanted from the cell pellet through an upper port without disturbing the pellet, obviating the need for careful supernatant removal procedures. Moreover, the tube design is such that even "lighter" cells present in the upper portion of the cell pellet are retained during the decantation process.

This tube and process provide the advantages of (i) a closed system for sterile manipulation of transfer of materials into and out of the tube, (ii) a design that allows for thorough decantation of the cell supernatant by inversion of the tube, without appreciable or differential loss of the cells at the top of the pellet. This latter feature of the invention facilitates high yield recovery of rare cells that might otherwise be lost or at least severely depleted during the washing process.

These and other features of the invention are described in the sections which follow.

SUMMARY OF THE INVENTION

In one aspect, the invention includes a cell washing device. According to an important feature of the invention, device is designed and constructed to allow for decantation by inversion of the supernatant from a cell pellet, without appreciable loss of cells from the pellet, and, importantly, without selective loss of the cells present in the upper portion of the cell pellet.

In one embodiment, the cell washing device includes an elongate centrifuge tube having generally cylindrical side walls and a conical bottom. According to an important feature of the invention, the conical bottom forms an apical angle of between about 50 and about 90°. The device also includes a lid sealed to the top of the tube, and the lid includes at least two access ports positioned and constructed for flow of liquid or gas therethrough.

In a particular embodiment of the invention, the access ports include (i) a liquid passage port adapted for sterile passage of liquid into and out of the tube, and (ii) an air vent capable of providing filtered air to the interior of the tube. In one embodiment, the device includes a ridge encircling the inlet port and said air vent.

In another embodiment, the lid of the cell washing device includes a concave lower portion adapted to funnel liquid from the tube into the liquid passage port when the tube is held in an inverted position. The liquid passage port may include a "LUER-LOK" connector. According to a related embodiment, the liquid passage port may communicate with a conduit tube which extends into the tube. A third port may be added to the lid of the device. In still another embodiment, this additional port is adapted to serve as an air vent for supporting culture of cells in the device, where the device also includes cell culture medium. The device may also include a support adapted to maintain the tube in an upright position.

In further related embodiments, the lower inner portion of the tube of the device is designed and adapted to promote retention of pellet in the lower portion of the tube. Various examples of retention means are illustrated. Such means include, but are not limited to, texturing on the inner surface walls of the lower portion of the tube, the presence of ridges on or grooves in the lower portion, the presence of fins projecting from the sides toward the center of the tube, the presence of longitudinal dividers in the lower portion of the tube, combinations of the foregoing, and the like.

In a related aspect, the invention includes a method of removing unwanted media from an isolated cell fraction. Typically, the cell fraction is a rare cell fraction, that is a fraction of cells that constitutes less than about 1% of the initial cell suspension. According to an important feature of the invention, by using the cell washing device described above, wash supernatant can be removed from a cell pellet in the tube, without appreciable or substantial loss of cells, by inverting the washing device for a period of time of at least one minute and as long as three minutes, in order to thoroughly drain the supernatant from the tube. Importantly, the device inhibits loss of cells that are "light" compared to the rest of the cell pellet and thus remain at the top of the pellet after centrifugation.

The washing method includes the following steps: (i) adding a suspension containing isolated cells to a centrifugable cell washing device as described above, (ii) washing the cells by the steps of: (a) centrifuging the cells at a sufficient force and for a sufficient period of time to form a supernatant and a cell pellet in the device, and then (b) removing supernatant by inverting the tube, and then (c) resuspending the cell pellet in a sterile diluent. The foregoing steps may be repeated as required according to the washing protocol determined by the practitioner. Particular cell types whose yields after washing are specifically enhanced include isolated $CD34^+$ hematopoietic progenitor cells and dendritic cells.

In still another related aspect, the invention includes an improved method for isolating and washing cells that have been separated in a "cell-trap" tube, referring particularly to the centrifugable tube disclosed by U.S. Pat. No. 5,474,687 and U.S. Pat. No. 5,663,051. According to this method, the cells of interest are first collected in an interface above a density gradient material fraction in the specialized cell-trap tube. The interface and cells therein are then transferred to a centrifugable washing tube according to the present invention, as described above. Cells are washed by the steps of (i) centrifuging at a sufficient force and for a sufficient period of time to form a supernatant and a cell pellet in the tube; (ii) removing the supernatant by inverting the tube; and (iii) resuspending the cell pellet in a sterile diluent. The foregoing steps may be repeated as required, according to a protocol specific for the particular selected cells.

$CD34^+$ hematopoietic progenitor cells and progenitor cells are advantageously washed using this particular set-up and procedure.

These and other objects and features of the invention will become more fully apparent when the following detailed description of the invention is read in conjunction with the accompanying drawings.

BRIEF DESCRIPTION OF THE FIGURES

FIGS. 2A and 2B show top and bottom views of a lid used in the device of the invention;

FIG. 3 shows a sectional view of an elongate form of the tube portion of the device having stabilizing fins;

FIGS. 11A–11D shows various views of an alternate embodiment of the invention, which includes circumferentially arranged longitudinal fins inside the lower portion of the tube; and FIGS. 12A–12C shows various views of an alternate embodiment of the invention, which includes dividers that form a plurality of compartments in the lower apical region of the tube.

DETAILED DESCRIPTION OF THE INVENTION

The invention is directed to a centrifugable tube that is particularly suited for washing cells.

I. Definitions

"Isolated cells" refers to cells that are substantially enriched from a cell suspension; by substantially enriched is meant that such isolated cells are present as a fractional portion of total cells in a cell mixture that is at least 1.5 and preferably at least two times greater than the fractional portion they constitute of the cell suspension from which they are isolated.

"Rare cells" refers to cells that constitute less than or equal to about 1% of total cells in a cell mixture. Examples of rare cells include $CD34^+$ hematopoietic progenitor cells, which constitute about 1% of white blood cells, natural killer cells, dendritic cells, cytotoxic T lymphocytes, natural suppressor cells, mesenchymal cells, and the like. These rare cell types are recognized in the art and are described, for example, in Male, D., et al. (*ADVANCED IMMUNOLOGY*, Mosby/Times Mirror International Publishers Ltd., London, 1996). In the context of the present invention, the term also encompasses tumor cells and nucleated fetal cells present in the blood at such abundance levels.

"Apical angle" refers to the angle formed at the apex of a tube of the invention. Such an angle can be measured by viewing the apical region of the tube in crossection and measuring the angle formed by the joining walls or extensions of the walls, in the case that the walls do not form a sharp angle at the apex.

II. Centrifugable Cell Washing Device

Figure 1:
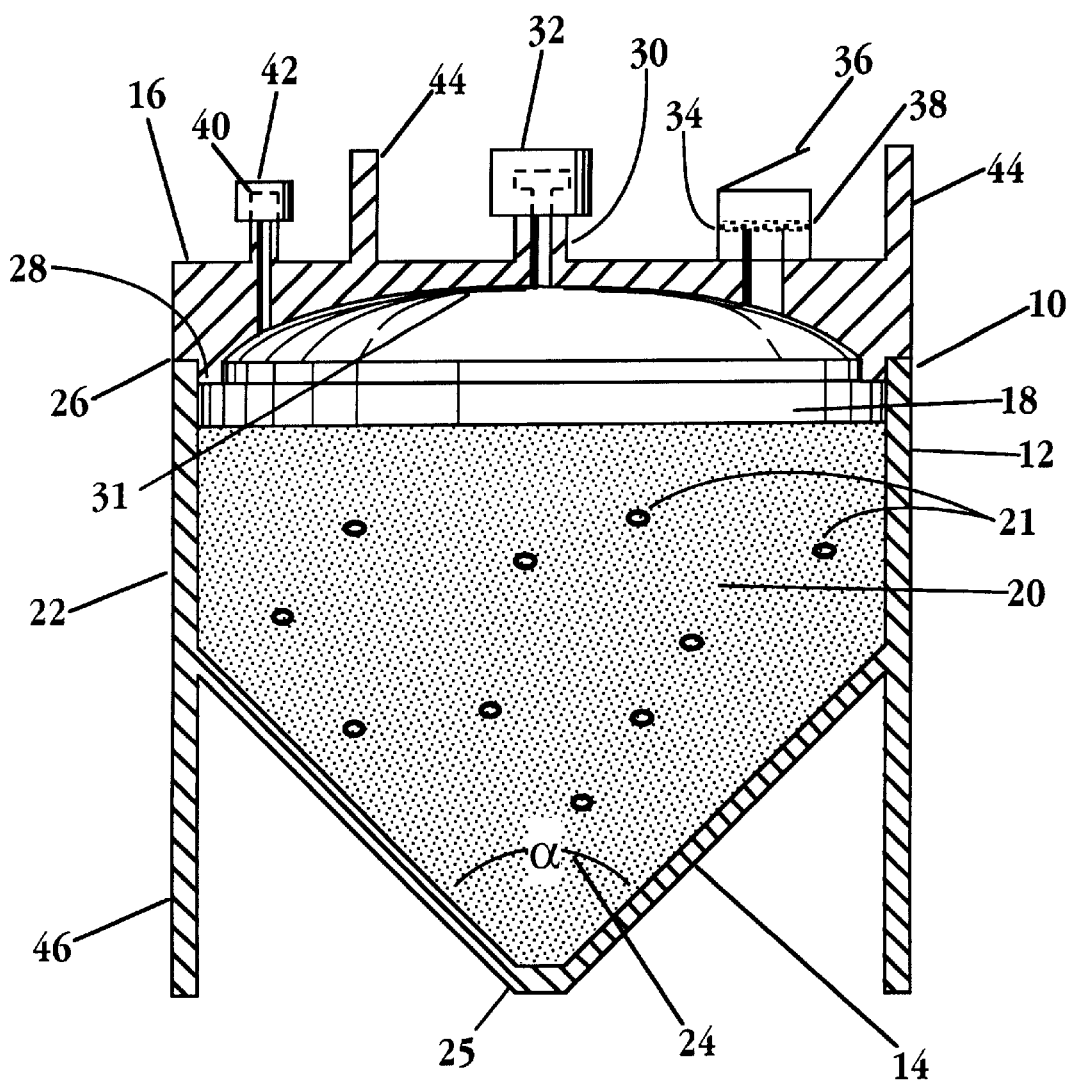
FIG. 1 shows a schematic crossectional view of a washing device of the invention.

FIG. 1 shows a schematic crossectional drawing of one embodiment of a centrifugable washing device of the invention. As illustrated, centrifugable washing device 10 is formed from elongate tube 12 having conical bottom region 14 and is sealed by fitted lid 16. Although the fitted lid can be attached to the tube by any means that provides a leak proof seal, as illustrated in FIG. 1, lid 16 is welded or bonded to tube 12.

Tube 12 is generally cylindrical in shape and forms an interior region 18 for containing biological materials, such as cells 21 in cell suspension 20. The tube can be formed from any material that is able to withstand repeated high centrifugal forces (up to about 10,000×g), and is preferably formed from a medical grade plastic commonly used in the field of centrifugation, such as polyallomer, polycarbonate, polyethylene, polypropylene, polystyrene, polysulfone, polytetrafluoroethylene ("TEFLON"), and the like. Preferably the material will also be medical grade material which is compatible with and not toxic to the biomaterials/cells to be processed in the tube.

Side walls 22 of tube 12 have a thickness that suits the material from which the tube is formed; a thickness between 0.5 and 5 millimeters (mm) is preferred for tubes formed of medical grade plastics, such as those mentioned above. Further, the material and thickness must be able to withstand centrifugal forces of at least 100×g, and preferably as high as 1,000×g.

An important feature of the device is the lower portion of tube 12 which forms conical bottom 14. In experiments carried out in support of the present invention, it has been determined that a wash supernatant can be removed by decantation of the tube without appreciable loss of cells into the discarded supernatant, when the conical bottom of the tube forms an apical angle, shown as angle ($\alpha$) 24, that is between about 50 and 90°. When apical angle 24 is within this range, it is possible to remove wash supernatant by inverting the tube for up to three minutes, without appreciable loss of rare cell types, and, according to an important feature of the invention, without appreciable loss of cells having relatively low densities. Lower apex 25 is flattened, so that the lower inside portion of the container does not end in a sharp conical angle.

According to another important feature of the invention, centrifugal washing device 10 includes lid 16 that is sealably fitted to top 26 of tube 12. As illustrated, rim 28 on lid 16 closely fits the interior circumference of top 26 of the tube to form a tight seal. It is appreciated that there are a number of ways in which lid 16 might be sealed to tube 12, such as by a threaded connection or an interior seal, such as an O-ring. Alternatively, lid 16 can be molded as an integral part of tube 12. Other sealing means, such as glues or welding may also be used to bond lid 16 to top 26 of tube 12.

Lid 16 includes at least two ports—an inlet/outlet port and a venting port. These ports are each capable of providing a sterile conduit for passage of material (liquid or gas, respectively) into or out of the tube. In the embodiment illustrated in FIG. 1, three ports are included. Port 30 is an inlet/outlet port capable of providing a sterile communication for passage of liquids into and out of the tube. Port 30, as illustrated, is located at the center of lid 16; however, it may be located anywhere in the lid. As shown, port 30 includes a "LUER-LOK" connector, and is used to introduce the original cell suspension and subsequent washing liquids into the tube. As illustrated, lower inner surface 31 of lid 16 is concave upward toward the center of the lid just underneath port 30. This feature of the lid facilitates decanting of liquids from the tube by funneling liquid toward port 30 when the tube is inverted. Cap 32 is provided to prevent introduction of contaminating materials to the tube during non-transfer conditions.

Second port 34 is an air vent that enables air to flow into or out of tube 12, as liquid sample is decanted from or added to the tube, respectively. Port 34 is covered with cap 36 during non-transfer conditions and may preferably include an air filter, such as microfilter 38, to prevent airborne contamination from entering the tube under air flow/ fluid transfer conditions.

Port 40 is an additional port that may be provided for ease of decantation of liquids from the tube or for a gas exchange vent. This gas exchange feature is particularly useful, when the device is used to culture cells, according to one embodiment of the present invention. This embodiment is particularly useful and convenient for use with cells, such as dendritic cells or hematopoietic progenitor $CD34^+$ cells, that require a culturing or growth step following isolation and prior to use.

Figure 4:
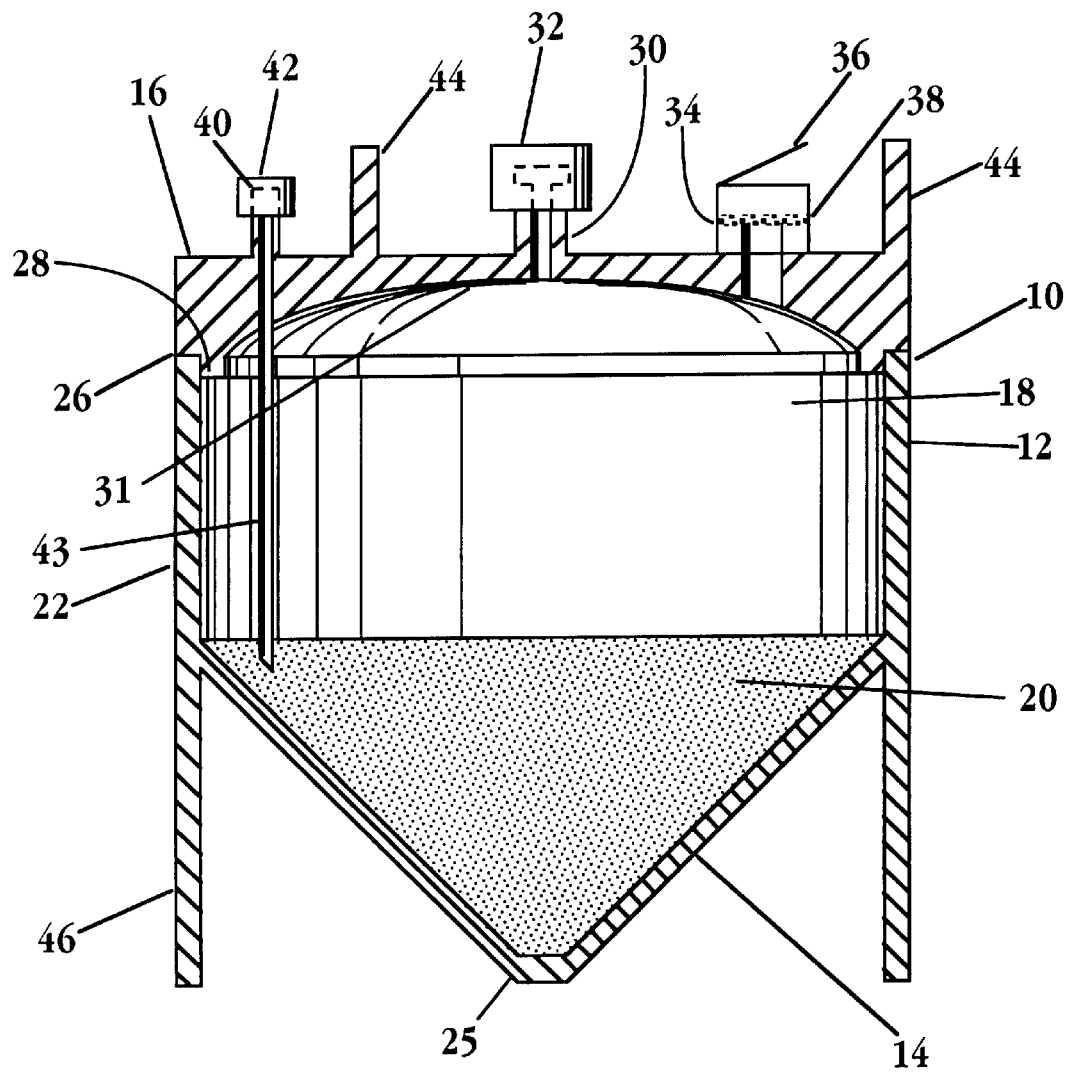
FIG. 4 shows an alternate embodiment of the washing device, which includes a conduit for decantation of contents.

FIG. 4 shows an alternate embodiment of the washing device illustrating a conduit 43 in communication with port 40 which facilitates ease of removal of the contents of the device, without the need for decantation. Conduit 43 can be made of a plastic material, or a flexible tubing, such as a TEFLON tubing, or can be a metal tube, and can be varied in length, or of variable length, according to the needs of the user.

When used as a cell culture vessel, the centrifugation device will preferably be formed of a plastic suitable for cell growth, such as polystyrene, polycarbonate, polytetrafluorothylene (PTFE; TEFLON), with such coatings or treatments known to promote cell growth. After washing, the cell suspension medium will generally be a physiological culture medium, such as Earle's complete medium, supplemented as appropriate to the cell growth requirements. In this embodiment, the centrifugation device may be adapted with additional features, such as a removable lid and/or an adaptor for spinner culture.

Returning to the device shown in FIG. 1, lower surface 31 of lid 16 may be adapted along the lines described above to provide a concave funneling path for flow of liquid toward port 40. Cap 42, shown covering port 40, is placed on the port when the port is not in use, to help maintain the sterility of cell suspension 20.

Also illustrated as part of lid 16 is axial ridge 44 which encircles a portion of the top of lid 16. Axial ridge 44 provides support for additional sterile shielding of the ports. In one embodiment, illustrated in FIG. 2A, ridge 44 circumscribes the portion of lid 16 that includes vent port 34 and sample introduction port 30, to provide support for a partial cover for this region. FIG. 2B shows a lower view of lid 16 showing lower surface 31 having openings 58, 60 and 62 corresponding to ports 30, 34 and 40, respectively.

Returning to the lower portion of tube 12 illustrated in FIG. 1, the device as illustrated includes base support 46 designed to provide a stable base support for the device so that it can be placed on a level surface without need of a special support container. In one embodiment, such a support will take the form of radial fins. FIG. 3 shows a crossectional view of lower portion of tube 50 of the device having radially positioned fins 52 and 54 shown in crossection at the viewing plane, and fin 56 shown in outline at the back portion of the device. Fins may be either flat or convex, as illustrated. Convex fins provide for enhanced mixing using a vortex mixer.

Figure 5:
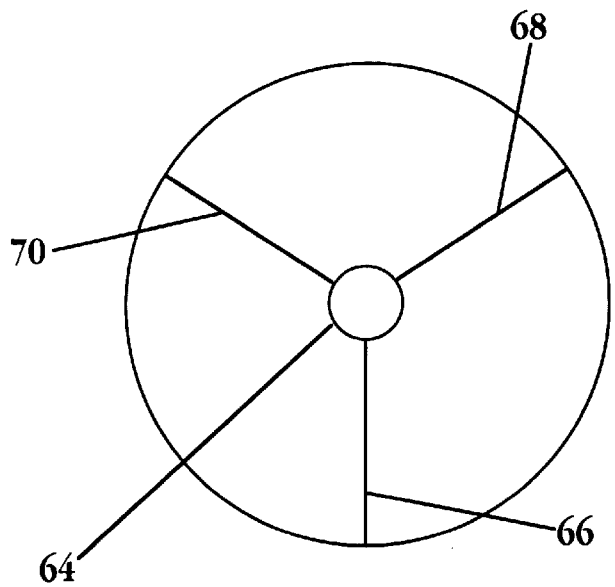
FIG. 5 shows a schematic view of the bottom of a tube with exterior fins.

FIG. 5 shows a lower view of the apex of a tube formed in accordance with the invention. Lower apex 64 is shown as a flattened portion of the tube at the lower extent of the tube; radiating from apex 64 are fins 66, 68 and 70.

Further embodiments of the washing device are illustrated in FIGS. 8–12. These embodiments generally promote better and/or more efficient segregation of the pellet from the supernatant during the washing process.

Figure 8A:
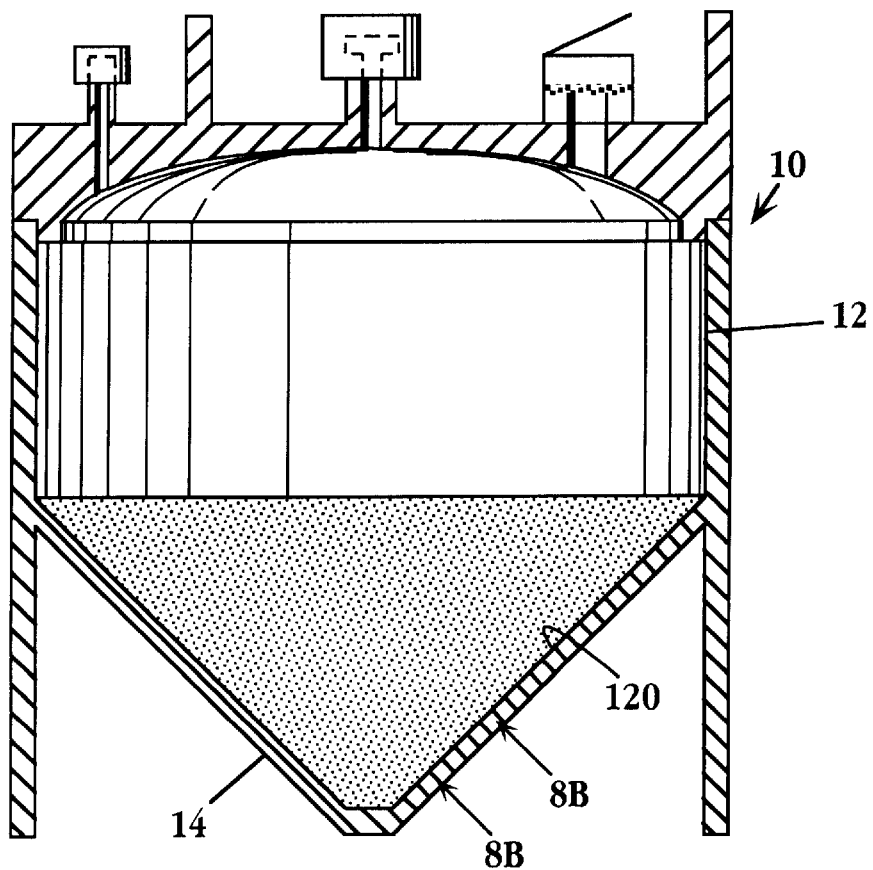
FIGS. 8A–8D show various views of an alternate embodiment of the device of the invention that includes a textured interior surface in the bottom portion of the tube.
Figure 8B:
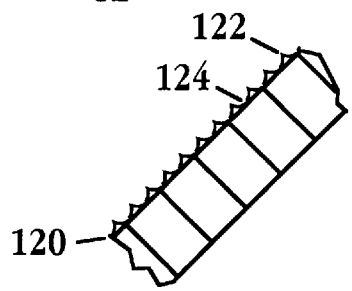

FIG. 8A shows washing device 10, in accordance with the invention having conical bottom region 14. According to this embodiment, inner surface 120 is textured, as illustrated in the cross sectional view of a segment of the bottom region 14 shown in FIG. 8B. Without committing to any particular theory, it is observed that such texturing improves retention of the pellet in the tube during removal of the supernatant.

The degree of roughness in such texturing may vary considerably and is characterized by the presence of "peaks" such as peak 122, and "valleys", such as valley 124, as illustrated. The peak to valley depth can range considerably, from about 0.8 to about 500 micrometers. Such texturing may be created by any of a number of methods known in the art, particularly in the arts relating to plastic molds. For example, a molded tube may be cast in a textured mold, which then imparts to the tube a textured, irregular surface. Means for making a textured mold are well known in the art, but generally involve etching the mold, by chemical or physical means, such as discussed below. Alternatively, the inner surface of the tube may be coated to provide a textured coating.

Representative etching means include bead blasting of the mold cavity, electron discharge machining of the mold cavity and chemical etching of the mold cavity. Etched metal molds suitable for forming textured tubes are made in a number of ways, known in the art, or can be contracted through a commercial mold supplier, such as Roehlen Industries (Walnut, Calif.). One conventional means for creating such a mold is to "bead blast" the cavity of the mold. This process removes small pockets of metal from the mold surface by hitting the surface with high velocity particles, such as particles of sodium bicarbonate (baking soda). Generally, the relief or depth of etching is determined by the grit of the particles used in this process; for example, aluminum oxide can produce mold etching depths of from about 0.8–2 $\mu$m. An etched mold surface can also be formed by an electron discharge machining (EDM) procedure that removes small pockets of metal from the mold by bombarding it with arcs of electricity. Such an etched mold produces a tube interior characterized by small protrusions of corresponding heights.

The mold may also be etched by chemical etching means. Generally, according to methods well known in the molding arts, a mask is placed on the mold surface in the area of texture. The mold is then dipped into an acid bath which removes metal from the unmasked areas. This process may be used to produce a highly dense irregular surface pattern on the mold surface, having etching depths ranging from about 1 to about 4 $\mu$m. This is a particularly effective and controlled means of producing an outer tube texture, in accordance with the present invention.

Figure 8C:
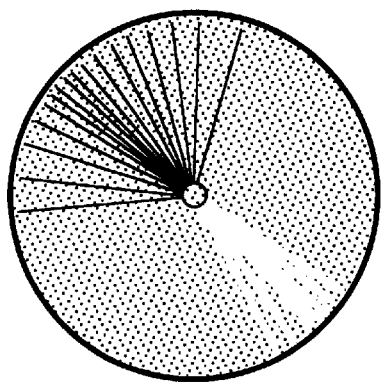
Figure 8D:
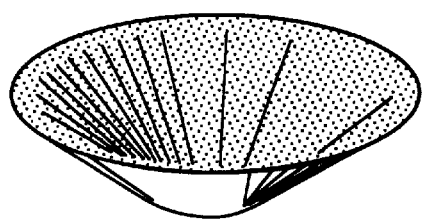

FIGS. 8C and 8D show alternate views of the textured bottom portions 14 of the washing device.

Figure 9A:
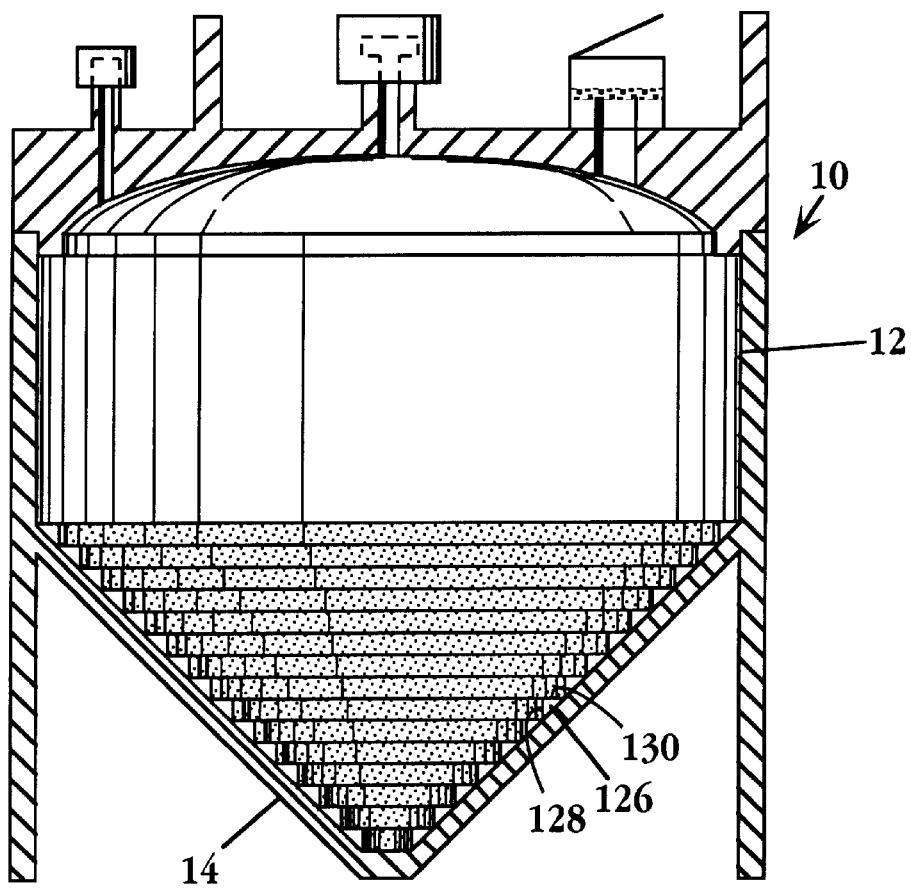
FIGS. 9A–9C show various views of an alternate embodiment of the device of the invention that features concentric steps or ridges in the bottom portion of the tube.
Figure 9B:
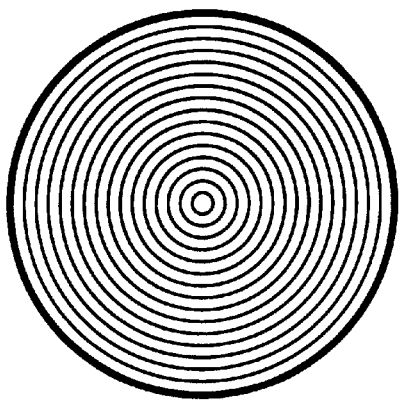
Figure 9C:
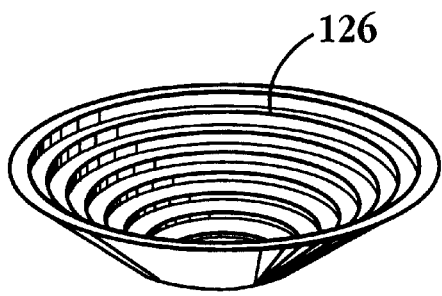

FIGS. 9A–9C show another embodiment of the washing device adapted to promote retention of the pellet and to enable processing of larger numbers of cells in conical bottom 14 of tube 12 during the washing process. In this embodiment, the interior surface of conical bottom 14 is provided with concentric ridges or "steps", such as ridge 126 having vertical surface 128 and horizontal surface 130. While illustrated as a conventional 90° step having vertical and horizontal surface that are roughly equal in dimension, it is appreciated that other angles and surface ratios may be used. The dimensions of the ridges may vary; generally, such the horizontal and vertical surfaces will extend between about 0.2 and 1.0 millimeter from the inner surface of the tube.

Figure 10A:
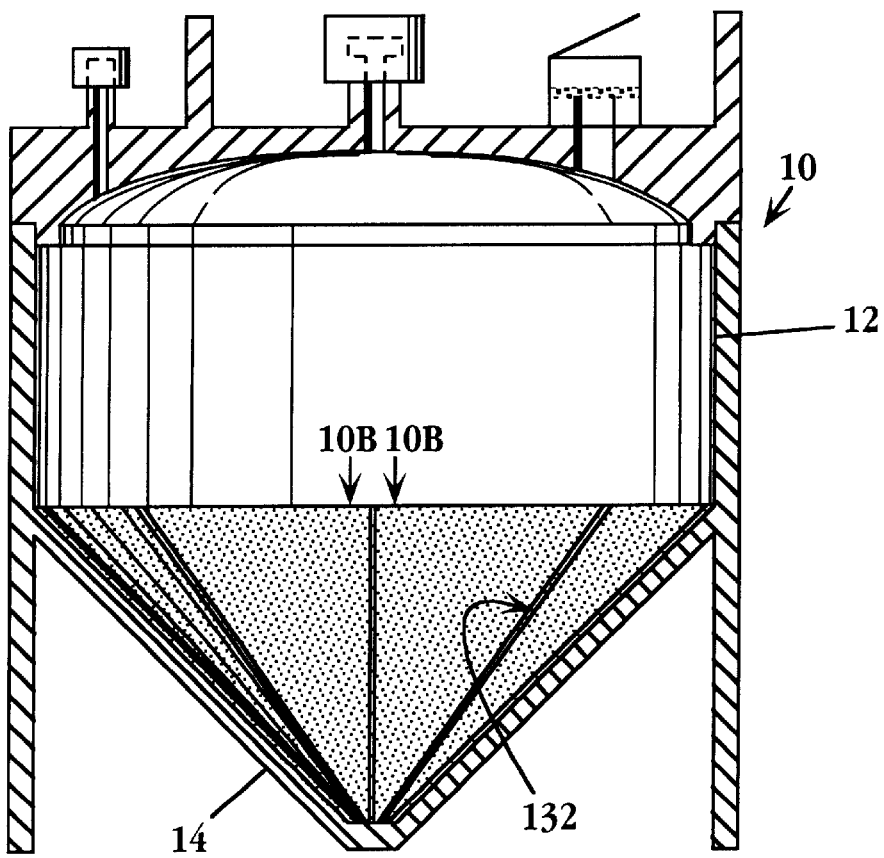
FIGS. 10A–10D show various views of an alternate embodiment of the device of the invention in which the inner lower surface of the tube forms grooves radiating from the lower apical region.
Figure 10B:
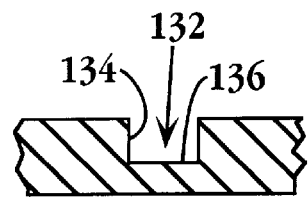
Figure 10C:
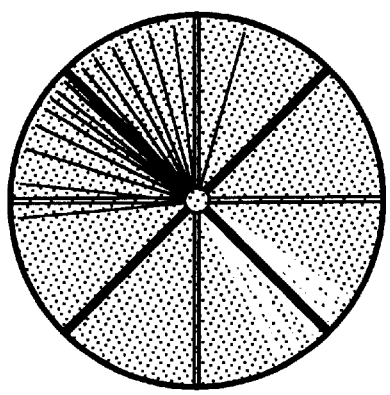
Figure 10D:
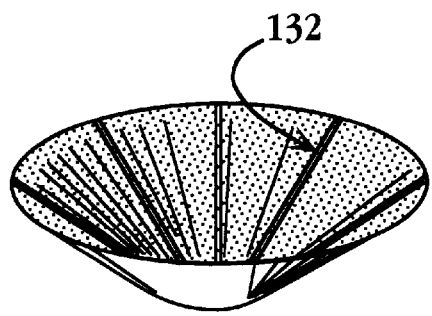

FIGS. 10A–10D illustrate another embodiment of the invention, in which the interior surface of conical bottom 14 forms a plurality of grooves or slots, such as groove 132, radiating from the central apex region. FIG. 10B shows a cross-section of a segment of sidewall 14, as indicated, showing groove 132, formed by sidewalls 134 and optionally lower surface 136. It is appreciated that sidewalls 134 could alternatively form a V-shaped groove. FIGS. 10C and 10D show additional views of bottom portions 14 of the device. Such grooves will generally have depths between about 0.2 and 1.0 millimeter.

FIGS. 11(A–D) show still another embodiment of the device in which lower portion 14 is augmented with a plurality of longitudinal fins, such as fin 134, that are positioned and designed to compartmentalize the lower, inside apical portion of the tube and to promote retention of the pellet in the conical lower surface of the tube. FIG. 11B shows a crossection across a fin, and FIGS. 11C and 11D show alternate views of the lower conical portion of the tube.

FIGS. 12(A–C) show still another embodiment of the invention, in which the lower portion 14 is fully compartmentalized with fins or dividers that extend across the inside diameter the tube, such as divider 136 transecting the lower region of the tube. As illustrated in the figure, four compartments are formed by two such dividers positioned at 90° angle one to another; however, it is appreciated that a series of dividers, such as radial dividers projecting from the center line of the tube, or a grid of dividers, may accomplish the same function. Again without committing to any underlying mechanism, such compartmentalization is constructed and designed to promote retention of the pellet in the lower portion of the tube.

The embodiments of the device described above can be used to advantage in washing cells isolated from biological fluids, such as are used in therapeutics. One advantage of the device is its ability to provide sterile transfer of liquids before, during and after the cell washing process. An unexpected advantage is its ability to provide high yield recovery of certain rare cell types. In particular, as described in more detail below, it provides high yield recovery of "light" cells that reside at the top of the cell pellet following centrifugation.

III. Method of Washing Cells

This section describes a method of washing cells according to the present invention. When a rare population of cells, such as CD34$^+$ hematopoietic progenitor cells, is washed according to the methods described herein, there is very little, if any, loss of the cells. In contrast when conventional methods are used, and in particular, using centrifuge tubes having apical angles greater than 90°, such cells may be selectively lost during decantation. While not ascribing to any particular theory, it is believed that this ability to retain cells having lesser buoyant densities is due to the unique apical angle range described herein. As stated above, such angle should be between about 50 and 90°, and preferably between about 60 and 80°.

FIGS. 6(A–H) shows a schematic representation of the steps involved in CD34+ cell isolation and washing, using the washing tube of the present invention in conjunction with a "cell-trap" centrifugation device and method, as described in U.S. Pat. Nos. 5,474,687 and 5,663,051, both of which references are incorporated herein by reference in their entireties. Briefly, the cell-trap tube is adapted for collection of cells that migrate to the interface that forms when a cell solution is loaded onto a density gradient separation material. A special feature of the tube is a constriction member that is positioned and constructed to retain fluid in the bottom portion of the device below the constriction member when the device is inverted.

Hematopoietic progenitor CD34+ cells are representative of cells whose isolation and washing is particularly improved by use of the washing device and method of the present invention, particularly in combination with the cell-trap tube described above, since these cells constitute less than 1% of a peripheral blood cell population and have "light" buoyant densities relative to the other cells present in the isolated interface fraction. Such cells typically migrate to the top of the pellet during subsequent washing steps, as described below.

Figure 6A:
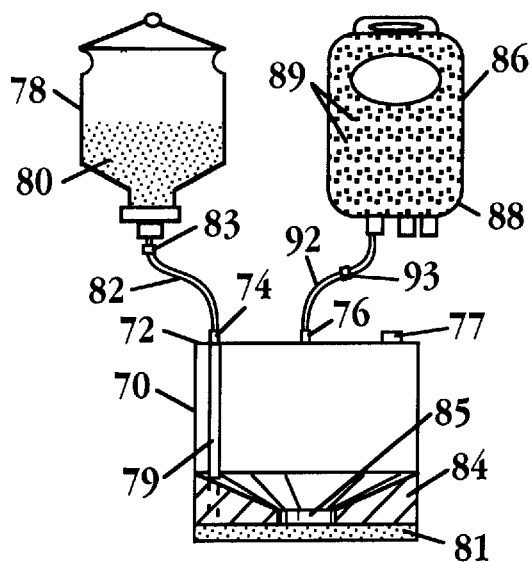
FIGS. 6A–6H show a scheme for washing cells according to the method of the invention.

Briefly, as shown in FIG. 6A, cell-trap centrifugation tube 70 having a closed top 72 and entry ports 74 and 76 is connected to first reservoir 78 containing density gradient medium 80. The density gradient medium may be of any composition, but has a well defined density which is calibrated according to the particular cell type to be isolated, as described in allowed U.S. patent application Ser. No. 08/570,397, incorporated herein by reference. As mentioned above, for isolation of CD34+ hematopoietic progenitor cells from a peripheral blood cell population, this density is preferably 1.0605±0.0005 gr/ml at 280 mOsm, and for isolation of CD34+ hematopoietic progenitor cells from bone marrow, the preferred density is 1.0685±0.0005 gr/ml at 280 mOsm. One exemplary density gradient material is an organosilanized colloidal silica composition, as described in U.S. Pat. No. 4,927,750, incorporated herein by reference, or such a composition further treated by addition of polyvinylpyrrolidone (PVP), as described in U.S. Pat. No. 5,789,148, incorporated herein by reference. It is appreciated that other density gradient materials may also be used, according to the specific protocol used for isolating a particular cell type.

Density gradient material 80 is added to the lower portion of cell-trap tube 70 through tubing 85 which is connected to tube 70 at port 74 via a sterile connection. Port 74 communicates with the lower portion of the tube through conduit 79. The gradient material 81 present in the bottom of the tube is added to a level extending to the top of opening 82 formed by constriction member 84 in the tube. Flow of gradient material is stopped by means of a valve, such as valve 83.

Figure 6B:
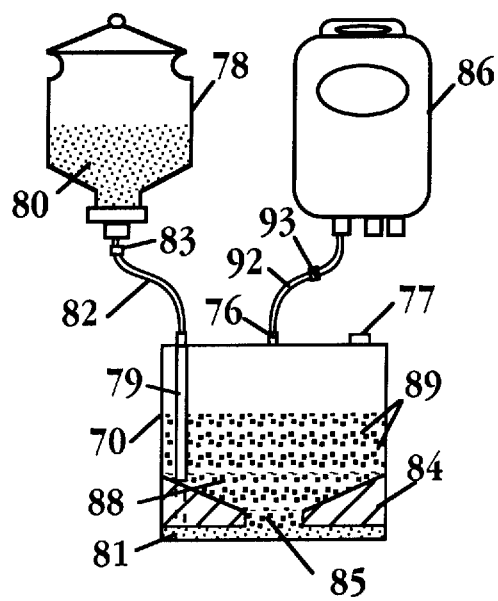

Also connected through a sterile connection with cell-trap tube 80 is cell reservoir 86, shown as a sterile blood collection "bag" in the figure. As shown in FIG. 6B, cell mixture 88 containing cells 89 flows through tubing 92 which communicates to cell-trap tube 70 through port 76 to fill or partially fill tube 70 in the region above constriction member 84. During this and all other additions, tube 70 may be vented by opening air vent 77.

Figure 6C:
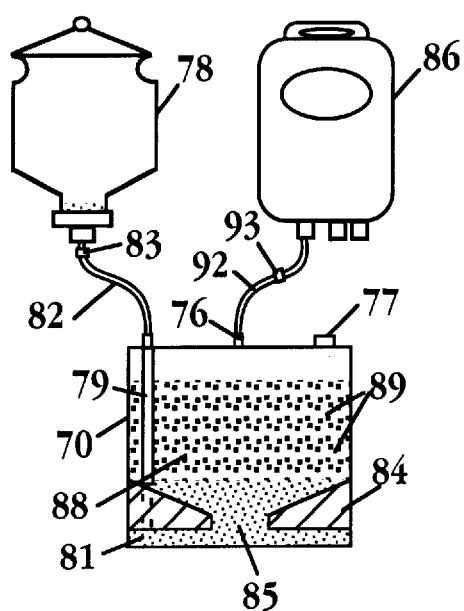

FIG. 6C illustrates a preferred step used to adjust the level of density gradient material in the tube to a level extending above the level of the constriction member. After the cell mixture as added, as described above, further gradient material is transferred from reservoir 78 into the tube by opening valve 83 between the reservoir and the tube. Gradient material flows through tubing 82 and through conduit 79 into the lower portion of the tube, to raise the level of the gradient material 81 in the tube to a level above constriction member 84.

Figure 6D:
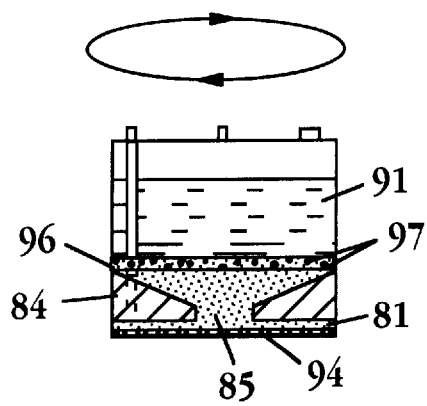

After addition of gradient material 81 and cell mixture 88 to the tube, reservoirs 78 and 86 and attached tubings 82 and 92 are detached from tube 70. FIG. 6D shows that the tube is then subjected to centrifugation at a rate sufficient to cause cells present in the cell mixture to distribute into the density gradient material 81 or into interface 96 that forms between density gradient material 81 and supernatant 96, according to the relative densities of the various cells present in the mixture. Centrifugation at a rate of 850×g for 30 min is generally sufficient for this purpose. During centrifugation, cells having specific densities greater than that of the density gradient material sediment to the pellet 94, while those cells, such as CD34+ cells, having specific densities that approximately the same as the gradient material concentrate at the interface region 96 formed between sample supernatant 91 and density gradient material 81.

It is now known that under the specific conditions described herein, using as the cell mixture a fraction derived from peripheral mononuclear cells and a density gradient material having a specific density of 1.0605 gr/ml, CD34+ cells concentrate in the interface region 96 (U.S. Pat. No. 5,474,687). Due to the cell-trap design of the tube, it is possible to transfer cells present in regions above opening 85 formed by constriction member 84 by inversion of tube 70, as illustrated in FIG. 6E without contamination of the resulting decanted product by cells in pellet 94.

Figure 6E:
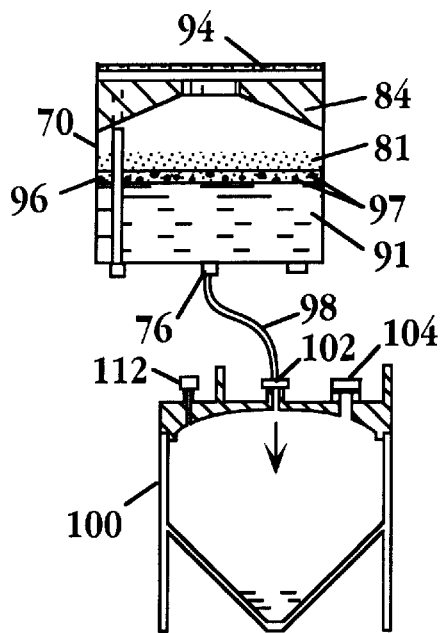

Referring further to FIG. 6E, decantation of cells can be effected in a sterile fashion by connecting port 76 to a sterile receptacle, preferably through a conduit, such as tubing 98. According to the improved method described herein, the sterile receptacle is wash tube 100, configured as described in Part II, above. As shown, tubing 98 connects to wash tube 98 through entry port 102. Supernatant 91 and interface 96 portions including CD34+ cells 97 drain through port 76 into tubing 98 and into wash tube 100. Air present in the tube may be vented through vent 104 during this process.

Figure 6F:
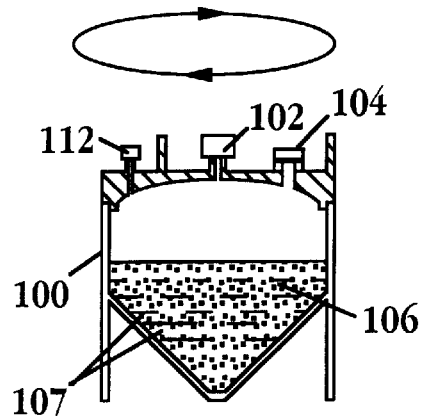
Figure 6G:
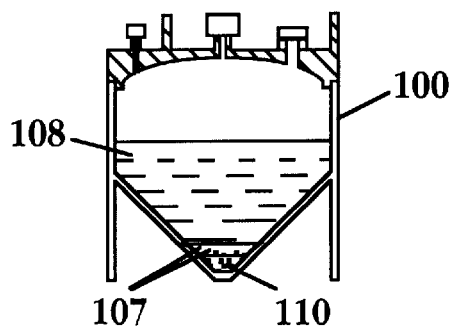
Figure 6H:
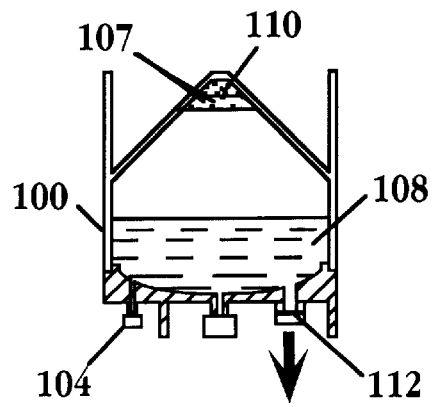

After supernatant and interface portions from cell-trap tube 70 are added to wash tube 100, tubing 98 is disconnected from the wash tube. Tube 100 is then centrifuged to pellet CD34+ cells of interest 107 from selected cell mixture 106 as illustrated in FIG. 6F. FIG. 6G shows wash tube 100 after centrifugation, where resulting pellet 110 contains CD34+ cells 107 in its upper portion, overlaid by wash supernatant 108. FIG. 6H shows removal of unwanted wash supernatant 108 by inversion of the tube. According to an important feature of the present invention, pellet 110, including light cells such as CD34+ cells 107, remains within wash tube 100 when the tube is inverted for up to three minutes, with little or no loss of cells. For further washing, cell pellet 110 can be resuspended in an appropriate volume of cell diluent, which is added to the tube through sterile entry port 102. The resuspended pellet can then be further washed, by further centrifugation and resuspension, as illustrated in FIGS. 5F–5H. It is appreciated that, depending on the cell type and nature of the original diluent, such washing may be varied in duration, repetition and buffer constituents. Such factors can be determined by the skilled practitioner in accordance with a specific washing protocol he or she determines to be most appropriate to the cells being washed.

Example 1 describes washing of a cell mixture enriched in CD34+ hematopoietic progenitor cells using the method described above. This example demonstrates an important aspect of the present invention—namely, that rare "light" cells, (e.g., those cells which sediment at the top of the cell pellet), such as the CD34+ cells illustrated above, which under the isolation conditions used typically occupy the upper strata of the wash pellet, are recovered in a yield of at least about 90% of their added amount, and preferably in a yield of about 95% of their added amount, using the device and method of the invention.

Figure 7:
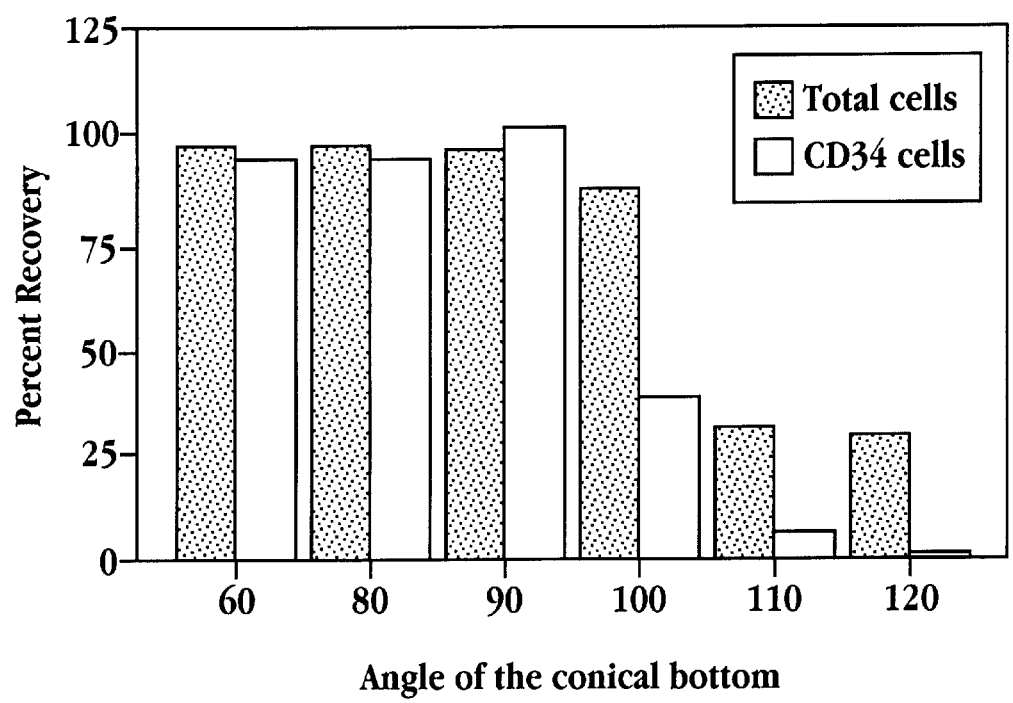
FIG. 7 shows the effects of varying apical angle on recovery of total cells (shaded bars) and $CD34^+$ cells (open bars)

Example 2 describes experiments carried out in support of the present invention, in which tube apical angles were tested for ability to retain CD34+ cells when the tube is inverted. The results of these experiments are shown in FIG. 7. These experiments demonstrate the importance of having an apical angle of between about 50 and about 90°, in order to provide a high yield of a rare cell type after a washing procedure. Specifically, as shown, when cells were washed in tubes having apical angles from 60–80°, greater than 95% of total and CD34+ cells were recovered after washing and decantation of cell supernatant by inversion of the wash tube. At an apical angle of 100°, there was selective depletion of CD34+ cells, resulting in recovery of only about 30% of these cells. At apical angles of 110 and 120, depletion of all cells was observed.

The foregoing studies illustrate one of the advantages achieved by the present invention—in the high (90–95%) recovery of "light" cells in a cell pellet, when a wash tube of the invention is used to wash the cells and the wash supernatant is decanted by inverting the tube.

The following examples illustrate, but in no way are intended to limit the present invention.

EXAMPLE 1

Washing of Isolated CD34+ Hematopoietic Progenitor Cells

CD34+ hematopoietic progenitor cells were isolated as described in U.S. Pat. No. 5,474,687 incorporated herein by reference, using as density gradient material an organosilanized colloidal silica (U.S. Pat. No. 4,927,750) adjusted to a density of 1.0605 gr/ml ("BDS") in a large scale cell-trap tube (ACT 300), such as described in U.S. Pat. No. 5,663,051, filed Dec. 11, 1995. Processing of the sample followed the general steps shown in FIGS. 5(A–H), as described above, with the following details: The cell trap separation tube was filled to a level just to the lower portion of the aperture constriction member with BDS. The blood sample was then added to the container. Additional BDS was then added (by addition through the conduit tube extending to the bottom portion of the tube, as illustrated) to bring the level of density gradient material to a level above the level of the constriction aperture. The tube was then centrifuged at 850×g for 30 minutes without braking. Following centrifugation, the device was connected via a sterile tubing to a washing device of the invention having an apical angle of 80° C. The sterile tubing was connected to a central sample inlet port in the lid of the washing device. An air vent in the washing device was opened, and the supernatant containing the interface was decanted into the washing device. The washing device was centrifuged at 850×g for 30 minutes without braking. The resulting supernatant was poured off via a decantation/outlet port in the lid of the washing device. Thereafter, the pellet was resuspended in calcium- and magnesium-free phosphate buffered saline (PBS), and the tube was then centrifuged at 850×g for 15 minutes. The resulting supernatant was decanted as described above, and the resulting pellet was resuspended in a pre-determined volume of PBS for quantitation of cells. Additional aliquots were used for FACS analysis of the cells.

EXAMPLE 2

Effect of Centrifuge Tube Apical Angle on Cell Recovery

Cells were isolated and transferred to wash tubes having different apical angles, (60°, 80°, 90°, 100°, 120°, as shown in FIG. 7) using the methods detailed in Example 1. For each pellet, total cells were quantitated; CD34+ cells were further quantitated by Fluorescent Activated Cell Sorting (FACS), according to standard methods well known in the art, using phycoerythrin-labeled anti-CD34+ monoclonal antibodies (Becton-Dickinson, Mountain View, Calif.).

Recoveries of total cells and CD34+ cells were quantitated by counting the number of cells in the starting and final materials and comparing these numbers.

While the invention has been described with reference to specific methods and embodiments, it will be appreciated that various modifications and changes may be made without departing from the invention.

It is claimed:

1. A cell washing device, comprising:
   (i) an elongate centrifuge tube having generally cylindrical side walls and a conical bottom wall, said conical bottom wall forming an apical angle of between about 50 and about 90° and having a wall-surface modification selected from the group consisting of
      (a) a plurality of longitudinal fins protruding inwardly from said side walls,
      (b) a plurality of longitudinal dividers defining a plurality of compartments,
      (c) a plurality of concentrically arranged ridges,
      (d) a plurality of grooves radiating from the apex region of said bottom wall, and
      (e) surface texturing; and
   (ii) a lid disposed at the top of said tube, said lid forming at least two access ports.

2. The cell washing device of claim 1, wherein said wall-surface modification includes a plurality of longitudinal fins protruding inwardly from said side walls.

3. The cell washing device of claim 1, wherein said wall-surface modification includes a plurality of longitudinal dividers defining a plurality of compartments.

4. The cell washing device of claim 1, wherein said wall-surface modification includes a plurality of concentrically arranged ridges.

5. The cell washing device of claim 1, wherein said wall-surface modification includes a plurality of grooves radiating from the apex region of said bottom wall.

6. The cell washing device of claim 1, wherein said wall-surface modification includes surface texturing.

7. The cell washing device of claim 6, wherein said surface texturing is characterized by peak to valley depths of between about 0.8 and 500 $\mu$m.

8. The cell washing device of claim 1, wherein said access ports formed by said lid include (i) a liquid passage port adapted for sterile passage of liquid into and out of said tube, and (ii) an air vent capable of providing filtered air to the interior of said tube.

9. The cell washing device of claim 8, wherein said liquid passage port forms a fluid connection with a conduit, said conduit extending into said tube.

10. The cell washing device of claim 8, wherein said lid includes a concave lower portion adapted to funnel liquid from said tube into said liquid passage port when said tube is in held in an inverted position.

11. The cell washing device of claim 8, wherein said liquid passage port further comprises an airtight connector for passage of sterile solutions into said tube.

12. The cell washing device of claim 8, which further includes a third port formed by said lid, said third port adapted to serve as an air vent for supporting culture of cells in said device, and a quantity of cell culture medium for supporting growth of cells.

13. The cell washing device of claim 8, which further comprises a ridge encircling at least said liquid passage port and said air vent.

14. A cell washing device, comprising:

an elongate centrifuge tube having generally cylindrical side walls and a conical bottom, said conical bottom forming an apical angle of between about 50 and about 90°, and a lid disposed at the top of said tube, said lid forming at least two access ports;

wherein said lid includes a concave lower portion adapted to funnel liquid from said tube into one of said access ports when said tube is held in an inverted position.

15. The cell washing device of claim 14, wherein said access ports formed by said lid include (i) a liquid passage port adapted for sterile passage of liquid into and out of said tube, and (ii) an air vent capable of providing filtered air to the interior of said tube.

16. The cell washing device of claim 15, wherein said liquid passage port forms a fluid connection with a conduit, said conduit extending into said tube.

17. The cell washing device of claim 15, wherein said concave lower portion of said lid is adapted to funnel liquid from said tube into said liquid passage port when said tube is held in an inverted position.

18. A cell washing device, comprising:

an elongate centrifuge tube having generally cylindrical side walls and a conical bottom, said conical bottom forming an apical angle of between about 50 and about 90°, and a lid disposed at the top of said tube, said lid forming at least two access ports including a liquid passage port and an air vent;

wherein said liquid passage port forms a fluid connection with a conduit, said conduit extending into said tube.

* * * * *